US008981176B2

(12) United States Patent
Taniguchi et al.

(10) Patent No.: US 8,981,176 B2
(45) Date of Patent: Mar. 17, 2015

(54) WATER-ABSORBING RESIN COMPOUND

(75) Inventors: Takayasu Taniguchi, Himeji (JP); Masayoshi Handa, Himeji (JP); Yasuhiro Nawata, Himeji (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 1024 days.

(21) Appl. No.: 12/956,563

(22) Filed: Nov. 30, 2010

(65) Prior Publication Data

US 2011/0068300 A1    Mar. 24, 2011

Related U.S. Application Data

(63) Continuation of application No. 10/552,152, filed as application No. PCT/JP2004/004989 on Apr. 7, 2004, now Pat. No. 7,868,075.

(30) Foreign Application Priority Data

Apr. 10, 2003 (JP) .................................. 2003-106308

(51) Int. Cl.
| A61F 13/15 | (2006.01) |
| A61L 9/01 | (2006.01) |
| C08L 101/14 | (2006.01) |
| A61F 13/84 | (2006.01) |
| A61L 15/42 | (2006.01) |
| A61L 15/46 | (2006.01) |
| A61L 15/60 | (2006.01) |
| B32B 27/18 | (2006.01) |

(52) U.S. Cl.
CPC ............ *C08L 101/14* (2013.01); *A61F 13/8405* (2013.01); *A61L 15/425* (2013.01); *A61L 15/46* (2013.01); *A61L 15/60* (2013.01); *A61L 2300/102* (2013.01); *A61L 2300/21* (2013.01); *A61L 2300/404* (2013.01); *A61L 2300/45* (2013.01); *B32B 27/18* (2013.01)
USPC ........................... 604/359; 604/360; 424/76.9

(58) Field of Classification Search
USPC ............................. 604/359, 360; 424/65, 76.9
See application file for complete search history.

(56) References Cited

U.S. PATENT DOCUMENTS

| 4,200,238 A | 4/1980 | Keyes et al. |
| 5,167,942 A | 12/1992 | Balkus et al. |
| 5,750,611 A | 5/1998 | Trouilhet |
| 6,277,772 B1 | 8/2001 | Gancet et al. |
| 6,469,080 B2 | 10/2002 | Miyake et al. |
| 6,703,451 B2 | 3/2004 | Hosokawa et al. |
| 6,855,134 B2 * | 2/2005 | Brooks .......................... 604/304 |
| 2003/0165546 A1 * | 9/2003 | Resch et al. ................... 424/401 |

FOREIGN PATENT DOCUMENTS

| CN | 1300803 A | 6/2001 |
| EP | 0257951 A2 | 3/1988 |
| JP | 2-253847 A | 10/1990 |
| JP | 8-052203 A | 2/1996 |
| JP | 8-127725 A | 5/1996 |
| JP | 2001-039802 A | 2/2001 |
| JP | 2001-505237 A | 4/2001 |
| JP | 2002-153545 A | 5/2002 |
| JP | 2002-537501 A | 11/2002 |
| JP | 2003-052746 A | 2/2003 |
| WO | 96/07437 A1 | 3/1996 |
| WO | 00/50098 A | 8/2000 |
| WO | 01/80914 A1 | 11/2001 |
| WO | 01/80915 A1 | 11/2001 |
| WO | 03/002089 A1 | 1/2003 |

OTHER PUBLICATIONS

Supplementary European Search Report of 04726264, dated Feb. 6, 2008.
International Search Report of PCT/JP2004/004989, mailing date Jul. 13, 2004.
Japanese Office Action dated Nov. 28, 2006, issued in corresponding Japanese Patent Application No. 2003-106308.
Chinese Office Action dated Mar. 2, 2007 of 2004800095576.

* cited by examiner

*Primary Examiner* — Melanie Hand
(74) *Attorney, Agent, or Firm* — Westerman, Hattori, Daniels & Adrian, LLP

(57) ABSTRACT

The object of the present invention is to provide a water-absorbing resin compound, wherein the water-absorbing resin compound can retain antibacterial properties of an antibacterial metal to suppress the emission of unpleasant odors even when an organic material exists in a system in the case of using an eluting-type antibacterial agent. Thus, the present invention relates to a water-absorbing resin compound, which comprises a water-absorbing resin, an antibacterial agent having a porous material incorporating an antibacterial metal, and a metal chelating agent. Further, the present invention also relates to an absorbing material, which comprises a water-absorbing resin compound of the present invention, and a hydrophilic fiber as well as an absorbing product, which comprises a liquid-permeable sheet and a liquid-non-permeable sheet, and an absorbing material comprising a water-absorbing resin compound of the present invention, and a hydrophilic fiber between the liquid-permeable sheet and the liquid-non-permeable sheet.

8 Claims, No Drawings

WATER-ABSORBING RESIN COMPOUND

CROSS-REFERENCE TO RELATED APPLICATIONS

This application is a Continuation of U.S. patent application No. 10/552,152, filed Oct. 7, 2005, now U.S. Patent No. 7,868,075, which is a national stage application filed under 35 USC §371 of International Application No. PCT/JP04/04989, filed Apr. 7, 2004, which claims priority of Japan Application No. 2003-106308, filed Apr. 10, 2003, the entire disclosures of which are hereby incorporated by reference.

FIELD OF THE INVENTION

The present invention relates to a water-absorbing resin compound. More specifically, the present invention relates to a water-absorbing resin compound which may be preferably used in absorbing products.

BACKGROUND OF THE INVENTION

Absorbing products are used in various fields of, for example, hygienic materials such as disposal diapers, sanitary napkins, incontinence pads and the like; urine-absorbing materials for pets; materials for city engineering and construction such as a packing material and the like; food freshness preservers such as drip absorbents, heat insulators and the like; agricultural materials such as water-retentive materials for soil and the like.

Especially for hygienic materials and the like, there is a problem that absorbing products which have absorbed a body fluid, in particular, urine, blood, sweat and the like, emit unpleasant odors. It is considered that these odors are putrid smells resulting from decomposition of body fluid components such as urea, proteins and the like with enzymes decomposing the body fluid components which are produced from bacteria ranging through skins and alimentary tracts. For urine, main components of these unpleasant odors are thought to be nitrogen-containing compounds such as ammonia, trimethylamine; sulfides such as hydrogen sulfide; methanethiols; aldehydes and the like.

In order to suppress emission of such unpleasant odors, absorbing materials containing odor adsorbents such as an active carbon, zeolite and the like (See, for example, JP-A 2001-37805 and JP-A 1999-512946), a water-absorbing material containing a water-absorbing resin and a germicide such as a quaternary ammonium salt which kills the above bacteria to prevent putrid smells from gradually increasing (See, for example, JP-A 2000-79159) are proposed. However, the absorbing materials containing odor adsorbents such as an active carbon, zeolite and the like are not effective against putrid smells which increase due to gradual decomposition of body fluid components. Furthermore, the water-absorbing material containing a water-absorbing resin and a germicide such as a quaternary ammonium salt is undesirable in terms of safety because it is possible that the germicide causes inflammation when it contacts with skins or mucous membranes.

Therefore, a compound containing a water-absorbing resin and an antibacterial agent having an inorganic compound incorporating an antibacterial metal such as silver, copper, zinc and the like is proposed (See, JP-A 2001-505237).

Antibacterial agents having an inorganic compound incorporating an antibacterial metal may be generally classified into two groups according to their expression manner of antibacterial properties based on a kind of an inorganic compound as a matrix; an eluting-type antibacterial agent which sustained-releases an antibacterial metal, and a non-eluting-type antibacterial agent which does not sustained-release an antibacterial metal. The eluting-type antibacterial agent expresses its antibacterial property by inhibiting enzymatic activities of microorganisms with eluted antibacterial metals. However, in this type of antibacterial agent, when an organic material exists in a system, the organic material forms salts with the sustained-released antibacterial metal to greatly reduce the antibacterial property. Therefore, in applications for absorbing a body fluid, for example, disposal diapers, sanitary napkins and the like, the eluting-type antibacterial agent has a disadvantage that its efficiency is reduced.

SUMMARY OF THE INVENTION

The object of the present invention is to provide a water-absorbing resin compound, wherein the water-absorbing resin compound can retain an antibacterial property of an antibacterial metal to suppress the emission of unpleasant odors even when an organic material exists in a system in the case of using an eluting-type antibacterial agent.

Therefore, the present invention relates to a water-absorbing resin compound, which comprises a water-absorbing resin, an antibacterial agent having a porous material incorporating an antibacterial metal, and a metal chelating agent.

In the water-absorbing resin compound according to the present invention, since the antibacterial agent having a porous material incorporating an antibacterial metal and the metal chelating agent coexist, the eluted antibacterial metal can immediately form a complex with the metal chelating agent. Therefore, even when an organic material exists in the system, the eluted antibacterial metal does not form salts with the organic material and, thereby, the water-absorbing resin compound can retain an antibacterial property of the antibacterial metal.

DETAILED DESCRIPTION OF THE INVENTION

A water-absorbing resin used in the present invention includes, for example, a cross-linked polymer of an acrylic acid salt, a cross-linked hydrolyzed product from a graft copolymer of a starch-acrylic acid salt, a cross-linked copolymer of a vinyl alcohol-acrylic acid salt, a cross-linked anhydrous maleic acid-graft-poly(vinyl alcohol), a cross-linked copolymer of isobutylene-anhydrous maleic acid, a cross-linked partially neutralized poly(acrylic acid), a saponificated copolymer of a vinyl acetate-acrylic ester and the like. Among them, a cross-linked polymer of an acrylic acid salt is preferably used because this polymer can absorb a large amount of water and hold absorbed water within its structure even when some loads are applied to this polymer.

A method for producing the water-absorbing resin includes a method known to a person skilled in the art such as a reversed phase suspension polymerization, an aqueous solution polymerization and the like. As the above water-absorbing resin, a commercially available cross-linked polymer of an acrylic acid salt such as a super absorbent polymer "AQUA KEEP" from SUMITOMO SEIKA CHEMICALS CO. LTD. can be used.

In addition, the antibacterial agent used in the present invention has a porous material incorporating an antibacterial metal.

An antibacterial metal includes, for example, silver, copper, zinc and the like. Among them, silver is preferably used because it is excellent in safety and antibacterial properties.

A porous material includes, for example, zeolite, silica gel, magnesium metasilicate aluminate, zirconium phosphate, calcium phosphate (apatite) and the like. Among them, zeolite is preferably used because it can easily elute an antibacterial metal.

The content of the antibacterial metal in the antibacterial agent is 0.1-15 parts by weight, preferably 0.5-10 parts by weight with respect to 100 parts by weight of the porous material. When the content of the antibacterial metal is less than 0.1 parts by weight, it is likely that a sufficient antibiotic property is not obtained. Further, when the content of the antibacterial metal is above 15 parts by weight, it is not economical.

A method of producing the antibacterial agent includes, for example, a method which comprises suspending a porous material in water and then adding an aqueous solution of an antibacterial metal to incorporate the antibacterial metal in the porous material. As the above antibacterial agent, a commercially available antibacterial agent such as an antibacterial agent "ZEOMIC" from SINANEN ZEOMIC CO., LTD. can be used.

The content of the antibacterial agent is 0.001-1 parts by weight, preferably 0.01-0.5 parts by weight with respect to 100 parts by weight of the water-absorbing resin. When the content of the antibacterial agent is less than 0.001 parts by weight, it is likely that a sufficient antibiotic property is not obtained. Further, when the content of the antibacterial agent is above 1 part by weight, it is not economical.

In addition, a metal chelating agent used in the present invention includes, for example, an aminocarboxylic acid metal chelating agent such as iminodiacetic acid, hydroxyethyl iminodiacetate, nitrilotriacetic acid, nitrilotripropionic acid, ethylenediaminetetraacetic acid, diethylenetriaminepentaacetic acid, triethylenetetraminehexaacetic acid, trans-1,2-diaminocyclohexanetetraacetic acid, N,N-bis(2-hydroxyethyl)glycine, diaminopropanoltetraacetic acid, ethylenediaminedipropionic acid, hydroxyethylenediaminetriacetic acid, glycoletherdiaminetetraacetic acid, diaminopropanetetraacetic acid, N,N'-bis(2-hydroxybenzyl)ethylenediamine-N,N-diacetic acid, 1,6-hexamethylenediamine-N,N,N',N'-tetraacetic acid and salts thereof; a polyphosphoric acid metal chelating agent such as pyrophosphoric acid, tripolyphosphoric acid, tetrapolyphosphoric acid, trimetaphosphoric acid, tetrametaphosphoric acid, and salts thereof. Among them, an aminocarboxylic acid metal chelating agent, in particular, ethylenediaminetetraacetic acid, diethylenetriaminepentaaceteic acid, triethylenetetraminhexaacetic acid, and salts thereof is preferably used because they can easily form a complex with the antibacterial metal to retain the antibacterial property of the antibacterial metal.

Additionally, when the metal chelating agent is used as a powder, 80 weight % or more of all particles have a particle size of but not limited to, preferably 100 μm or smaller because they can homogeneously disperse in a water-absorbing resin.

The content of metal chelating agent is 0.01-10 parts by weight, preferably 0.05-5 parts by weight with respect to 100 parts by weight of the water-absorbing resin. When the content of the metal chelating agent is less than 0.01 parts by weight, it is likely that the water-absorbing resin compound cannot retain the antibacterial property of the antibacterial metal. Further, when the content of the metal chelating agent is above 10 parts by weight, it is not economical because obtained effects are less than expected from the added amount.

The water-absorbing resin compound according to the present invention may be obtained by mixing a water-absorbing resin, an antibacterial agent, and a metal chelating agent. A method of mixing the water-absorbing resin, the antibacterial agent, and the metal chelating agent includes, for example, (a) a method which comprises mixing a powder of a water-absorbing resin, an antibacterial agent and a metal chelating agent; (b) a method which comprises adding a dispersion solution of an antibacterial agent and a solution of a metal chelating agent to a water-absorbing resin and then drying the mixture; (c) a method which comprises adding an antibacterial agent and a metal chelating agent to a solution of a monomer which polymerizes to form a water-absorbing resin, mixing them and then polymerizing the monomer; (d) a method which comprises adding an antibacterial agent and a metal chelating agent to a water containing gel of a water-absorbing resin and then mixing them and (e) a method which comprises adding an antibacterial agent and a metal chelating agent to a water-absorbing resin during or after drying the water-absorbing resin and then mixing them; and the like.

The absorbing material according to the present invention comprises the above water-absorbing resin compound and a hydrophilic fiber.

A hydrophilic fiber includes, for example, cellulosic fibers, artificial cellulosic fibers and the like. Additionally, the hydrophilic fiber may contain a hydrophilic artificial fiber to the extent not to obstruct the object of the present invention.

A preferable embodiment of the absorbing material includes, for example, a mixed dispersion obtained by mixing a water-absorbing resin compound and a hydrophilic fiber to form a homogeneous composition, a sandwich structure comprising a water-absorbing resin compound lying between two sheets made of hydrophilic fibers, and the like.

The absorbing material may contain an adhesive binder such as thermal fusible synthetic fibers, hot-melt adhesives, adhesive emulsion and the like in order to enhance retention of shape.

According to the present invention, the absorbing product may be produced by laying the absorbing material between a liquid-permeable sheet and a liquid-non-permeable sheet.

A liquid-permeable sheet includes, for example, a non-woven fabric of an air-through type, a spun bond type, a chemical bond type, a needle punch type and the like which are made of fibers of polyethylene, polypropylene, polyester and the like.

A liquid-non-permeable sheet includes, for example, synthetic resin films made of a resin such as polyethylene, polypropylene, poly(vinyl chloride) and the like.

The absorbing product according to the present invention can be preferably used for hygienic materials such as disposal diapers, sanitary napkins, incontinence pads and the like; urine-absorbing materials for pets; materials for city engineering and construction such as a packing material and the like; food freshness preservers such as drip absorbents, heat insulators and the like; agricultural materials such as water-retentive materials for soil and the like.

EXAMPLES

The present invention will be further described in detail below, but the following examples should not be construed as limiting the scope of the present invention.

Example 1

To 100 g of a water-absorbing resin (AQUA KEEP SA60S from SUMITOMO SEIKA CHEMICALS CO. LTD.) were added 0.1 g of an ethylenediaminetetraacetic acid disodium salt (85 weight % or more of all particles have a particle size of 100 μm or less.) and 0.025 g of a silver-zeolite antibacterial agent (ZEOMIC AJ10D from SINANEN ZEOMIC CO., LTD., silver content: 2.7 weight %), and mixed well to obtain 100.1 g of the desired water-absorbing resin compound.

Example 2

To a dispersion solution of 100 g of a water-absorbing resin (AQUA KEEP SA60S from SUMITOMO SEIKA CHEMICALS CO. LTD.) in 400 mL of n-heptane was added 0.25 g of a solution of a diethylenetriaminepentaacetic acid pentasodium salt (40 weight %) and then mixed well. Then, n-heptane was removed by distillation and dried to obtain 100.1 g of the water-absorbing resin.

To the resulting water-absorbing resin was added 0.025 g of a silver-zeolite antibacterial agent (ZEOMIC AJ10D from SINANEN ZEOMIC CO., LTD., silver content: 2.7 weight %), mixed well to obtain 100.1 g of the desired water-absorbing resin compound.

Example 3

Following the general procedures of Example 2, and making non-critical variations but using 2.5 g of the solution of a diethylenetriaminepentaacetic acid pentasodium salt (40 weight %), 101.0 g of the desired water-absorbing resin compound was obtained.

Example 4

Following the general procedures of Example 2, and making non-critical variations but substituting a solution of a triethylenetetraminehexaacetic acid hexasodium salt (40 weight %) (Clewat-TH from TEIKOKU CHEMICAL INDUSTRIES CO., LTD.) for the solution of a diethylenetriaminepentaacetic acid pentasodium salt (40 weight %), 100.1 g of the desired water-absorbing resin compound was obtained.

Example 5

Following the general procedures of Example 1, and making non-critical variations but using 4 g of the solution of an ethylenediaminetetracetic acid disodium salt (85 weight % or more of all particles have a particle size of 100 μm or less.), and using 0.1 g of a silver-zeolite antibacterial agent (ZEOMIC AJ10D from SINANEN ZEOMIC CO., LTD., silver content: 2.7 weight %), 104.1 g of the desired water-absorbing resin compound was obtained.

Example 6

Following the general procedures of Example 1, and making non-critical variations but using 2 g of the solution of an ethylenediaminetetracetic acid disodium salt (85 weight % or more of all particles have a particle size of 100 μm or less.), and using 0.4 g of a silver-zeolite antibacterial agent (ZEOMIC AJ10D from SINANEN ZEOMIC CO., LTD., silver content: 2.7 weight %), 102.4 g of the desired water-absorbing resin compound was obtained.

Comparative Example 1

A water-absorbing resin (AQUA KEEP SA60S from SUMITOMO SEIKA CHEMICALS CO. LTD.) 100 g was used without any treatment.

Comparative Example 2

Following the general procedures of Example 1, and making non-critical variations but without adding a solution of an ethylenediaminetetraacetic acid disodium salt, 100.0 g of the water-absorbing resin compound was obtained.

Comparative Example 3

Following the general procedures of Example 1, and making non-critical variations but without adding a silver-zeolite antibacterial agent, 100.1 g of the water-absorbing resin compound was obtained.

An ammonia generation suppression test and an organoleptic test for odor were carried out on the water-absorbing resin compounds obtained from the above Examples, and the water-absorbing resins or the water-absorbing resin compounds obtained from the above Comparable Examples according to the following manners.

(1) Production of an Absorbing Material

A mixture of 1 g of the water-absorbing resin compound or the water-absorbing resin and 1 g of ground pulp was formed onto 5 cm diameter tissue paper by air blowing. The tissue paper of the same size were layered and pressed by applying 145 kPa for 30 seconds to form a desired absorbing material.

(2) Ammonia Generation Suppression Test

Artificial urine was prepared by dissolving 25 g of urea, 9 g of sodium chloride, 0.6 g of magnesium sulfate heptahydrate, 0.7 g of calcium lactate, 4 g of potassium sulfate and 2.5 g of ammonium sulfate were dissolved in 1 L of distilled water. An urease solution was prepared by diluting 1000 times 1000 U/ml urease isolated from jack bean *Canavalia ensiformis* in 50% glycerin (MERCK & CO., INC.) with distilled water.

The resulting absorbing material obtained in the above manner was placed in a 100 mL Meyer flask, and the absorbing material was swollen by adding artificial urine with urease (prepared by mixing 30 g of the above artificial urine and 1 mL of the above urease solution). Immediately after addition of the artificial urine with urease, the flask was sealed with a rubber cap equipped with a gas detector tube (Ammonia 3D from GASTEC CORPORATION) which was then, stored at 30° C. After 3, 10 and 24 hours, the readings of the gas detector tube were recorded. The results are listed in Table 1.

TABLE 1

Ammonia Generation Suppression Test

| | Antibacterial Agent | Metal Chelating Agent | Readings of the Gas Detector Tube (ppm · hr) after: | | |
|---|---|---|---|---|---|
| | | | 3 hours | 10 hours | 24 hours |
| Example 1 | 0.025 | 0.1 | 0 | 10 | 25 |
| Example 2 | 0.025 | 0.1 | 0 | 10 | 25 |
| Example 3 | 0.025 | 1.0 | 0 | 0 | 10 |
| Example 4 | 0.025 | 0.1 | 0 | 10 | 25 |
| Example 5 | 0.1 | 4.0 | 0 | 0 | 0 |
| Example 6 | 0.4 | 2.0 | 0 | 0 | 0 |
| Comp. Ex. 1 | 0 | 0 | 0 | 50 | 150 |
| Comp. Ex. 2 | 0.025 | 0 | 0 | 30 | 100 |
| Comp. Ex. 3 | 0 | 0.1 | 0 | 50 | 150 |

(3) Organoleptic Test for Odor

To a 100 mL Meyer flask were placed 50 mL of fresh urine, 0.25 g of urea and 1 g of pulp sampled from a used disposal diaper. By standing this solution for 24 hours, a fermented urine was prepared. Since the fresh urine is sterile, it does not emit sufficient odor without inoculating a fermented urine. Therefore, a test solution was prepared by mixing the fresh urine and the above fermented urine at a ratio of 9:1 (w/w).

After the absorbing material obtained in the above manner was placed in a 250 mL glass bottle, the absorbing material was swollen by adding 30 g of the above test solution. Immediately after addition of the test solution, the bottle was sealed, and stored at 40° C. for 24 hours. Then, odor from the 250 mL glass bottle were evaluated by five persons (A-E) according to "six stage odor intensity" criteria as follows:

5: Intense odor;
4: Strong odor;
3: Easily perceiving odor;
2: Mild odor (possible to recognize the kind of odor);
1: Slight odor (possible to recognize the existence of odor); and
0: No odor.

The odors were scored with there average values. The results are listed in Table 2.

TABLE 2

Organoleptic Test for Odor

| | Antibacterial Agent | Metal Chelating Agent | Evaluation by five persons: | | | | | Average |
|---|---|---|---|---|---|---|---|---|
| | | | A | B | C | D | E | |
| Example 1 | 0.025 | 0.1 | 3 | 3 | 2 | 3 | 4 | 3 |
| Example 2 | 0.025 | 0.1 | 3 | 3 | 3 | 2 | 3 | 2.8 |
| Example 3 | 0.025 | 1.0 | 2 | 2 | 3 | 2 | 3 | 2.4 |
| Example 4 | 0.025 | 0.1 | 3 | 3 | 3 | 3 | 3 | 3 |
| Example 5 | 0.1 | 4.0 | 2 | 2 | 3 | 2 | 2 | 2.2 |
| Example 6 | 0.4 | 2.0 | 2 | 1 | 2 | 1 | 2 | 1.6 |
| Comp. Ex. 1 | 0 | 0 | 5 | 4 | 5 | 4 | 5 | 4.6 |
| Comp. Ex. 2 | 0.025 | 0 | 3 | 4 | 4 | 3 | 4 | 3.6 |
| Comp. Ex. 3 | 0 | 0.1 | 4 | 4 | 4 | 5 | 5 | 4.4 |

The values for the antibacterial agent and the metal chelating agent in Tables 1 and 2 are indicated in "parts by weight" with respect to 100 parts by weight of the water-absorbing resin.

As clearly understood from Tables 1 and 2, the absorbing materials using the desired water-absorbing resin compound according to Examples 1-6 maintain antibacterial properties of the antibacterial metal, and suppress emission of unpleasant odors even when organic materials exist in the system.

What is claimed is:

1. A water-absorbing resin compound, which is a mixture of a water-absorbing resin, an antibacterial agent comprising a porous material incorporating an antibacterial metal, and a metal chelating agent,
   wherein the water-absorbing resin consists of a cross-linked polymer of an acrylic acid salt;
   wherein the antibacterial agent is a silver-zeolite antibacterial agent,
   wherein the content of the antibacterial metal incorporated in antibacterial agent is 0.1-15 parts by weight with respect to 100 parts by weight of the porous material.

2. The water-absorbing resin compound according to claim 1, wherein the content of the antibacterial agent is 0.001-1 parts by weight with respect to 100 parts by weight of the water-absorbing resin.

3. The water-absorbing resin compound according to claim 1, wherein the content of the metal chelating agent is 0.01-10 parts by weight with respect to 100 parts by weight of the water-absorbing resin.

4. The water-absorbing resin compound according to claim 1, wherein the metal chelating agent is an aminocarboxylic acid metal chelating agent.

5. The water-absorbing resin compound according to claim 4, wherein the aminocarboxylic acid metal chelating agent is at least one selected from a group consisting of ethylenediaminetetraacetic acid, diethylenetriaminepentaacetic acid, triethylenetetaraminehexaacetic acid, and salts thereof.

6. The water-absorbing resin compound according to claim 1, wherein the antibacterial agent is an eluting-type.

7. An absorbing material, which comprises a water-absorbing resin compound according to any one of claims 1, 2, 3, 4, 5 and 6, and a hydrophilic fiber.

8. An absorbing product, which comprises a liquid-permeable sheet; a liquid-non-permeable sheet; and an absorbing material comprising a water-absorbing resin compound according to any one of claims 1, 2, 3, 4, 5 and 6 and a hydrophilic fiber, wherein the absorbing material lying between the liquid-permeable sheet and the liquid-non-permeable sheet.

* * * * *